US00PP36547P2

(12) United States Plant Patent
Hansen

(10) Patent No.: US PP36,547 P2
(45) Date of Patent: Mar. 11, 2025

(54) ***DELOSPERMA* PLANT NAMED 'Dancing Embers'**

(50) Latin Name: ***Delosperma* hybrid**
Varietal Denomination: Dancing Embers

(71) Applicant: Hans A Hansen, Zeeland, MI (US)

(72) Inventor: Hans A Hansen, Zeeland, MI (US)

(73) Assignee: Walters Gardens, Inc.

( * ) Notice: Subject to any disclaimer, the term of this patent is extended or adjusted under 35 U.S.C. 154(b) by 0 days.

(21) Appl. No.: 18/445,963

(22) Filed: Apr. 16, 2024

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./422
See application file for complete search history.

*Primary Examiner* — Susan McCormick Ewoldt

(57) ABSTRACT

A new and distinct cultivar of *Delosperma* plant named 'Dancing Embers' is disclosed, characterized by abundant, large, reddish-orange flowers with a reddish-purple eye and cream centers occurring throughout the plant. Plants have a low, mounding habit, and are tolerant to at least USDA zone 6 as well as high heat and drought conditions. The new plant is useful for its bright flowers and low habit in the landscape garden or as a container plant.

2 Drawing Sheets

Latin name of the genus and species: *Delosperma* hybrid.
Variety denomination: 'Dancing Embers'.

STATEMENT REGARDING PRIOR DISCLOSURES UNDER 37 CFR 1.77(B)(6)

The claimed plant was first sold or offered for sale by Walters Gardens, Inc. to Dallas Johnson Greenhouse, Inc. on Apr. 24, 2023, by Walters Gardens, Inc., who obtained the plant and all information relating thereto, from the inventor. Subsequently, on Dec. 1, 2023, the new plant was featured in a non-enabling disclosure of a brief description and photograph on a website operated by Walters Gardens, Inc. No plants of *Delosperma* 'Dancing Embers' have been sold in this country or anywhere in the world nor has any disclosure of the new plant been made more than one year prior to the filing date of this application, and such sale or disclosure within one year was either derived directly or indirectly from the inventor.

BACKGROUND OF THE INVENTION

The present invention relates to the new and distinct *Delosperma* cultivar named 'Dancing Embers' also referred to here as the new plant. 'Dancing Embers' was hybridized by the inventor at a wholesale perennial nursery in Zeeland, Michigan, USA as the result of a greenhouse cross between PJS01S (not patented) as the female parent and 'John Proffitt' (not patented) in the summer of 2019. Seeds from this pollination were collected in the fall of 2019 and were sown earlier the next year. The new plant originated from a single seedling, was initially evaluated in the summer of 2021, selected for further evaluation, and assigned the breeder code 19-5-8.

*Delosperma* 'Dancing Embers' has been successfully asexually propagated by shoot tip cuttings since 2021 at a wholesale perennial nursery in Zeeland, Michigan and found to produce identical stable and identical plants in successive generations of asexual propagation.

SUMMARY OF THE INVENTION

*Delosperma* 'Dancing Embers' differs from the parents as well as all other Hardy Ice Plant cultivars known to the inventor. The most similar known *Delosperma* cultivars include: 'PWWG02S' (not patented), 'PJS02S' (not patented), and 'P001S' (not patented).

'PWWG02S' has similar reddish-orange petals, but the petals are narrower with more space between, and the petal base is purplish-pink. 'PJS02S' has more orangish flower petals and the plant is not as winter hardy. 'P001S' has petals with a bright orange outer portion and a large magenta center.

The female parent, 'PJS01S', has petals that begin a bright rose and mature to fuchsia. The male parent, 'John Proffitt', has petals of a purplish-fuchsia.

*Delosperma* 'Dancing Embers' differs from the above cultivars and all other cultivars of Hardy Ice Plant known to the inventor with the following repeating distinguishing characteristics in combination:

1. Large flowers of bright reddish-orange flowers with reddish-purple eye and cream centers;
2. Low, mounded habit with good flower coverage, flowering on shoot tips and nodes;
3. Moderately evergreen, winter hardy to at least USDA Zone 6, and with good drought and heat tolerance;
4. Foliage takes on strong dark reddish color from late fall into spring.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
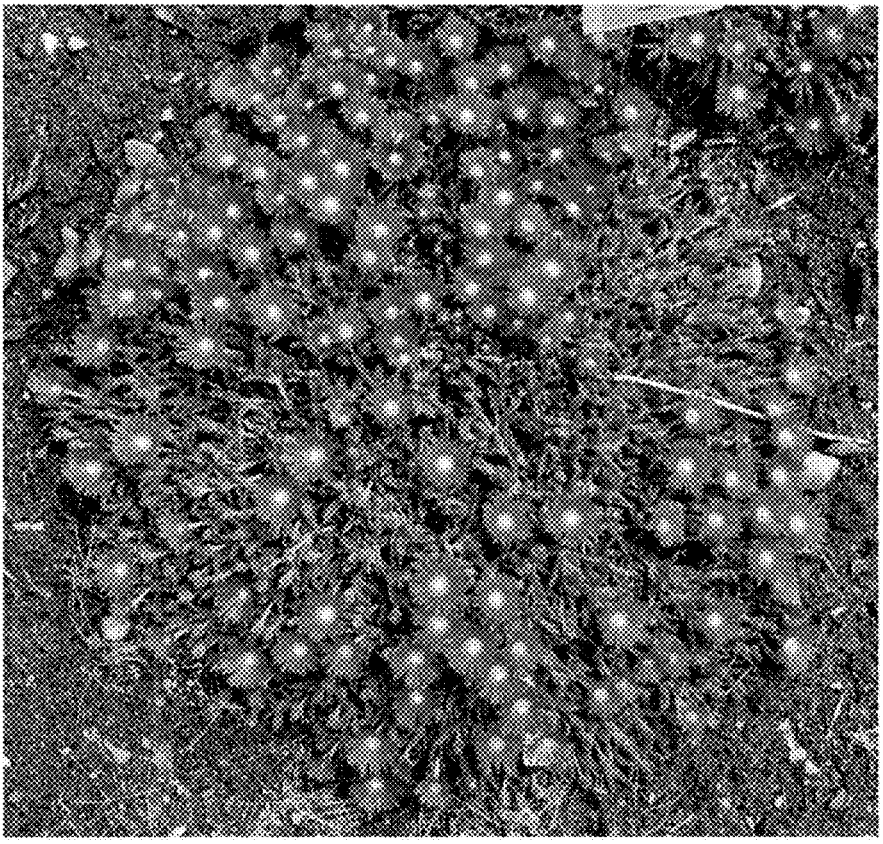
FIG. 1 shows the top-view habit of a two-year-old plant in early flowering.
Figure 2:
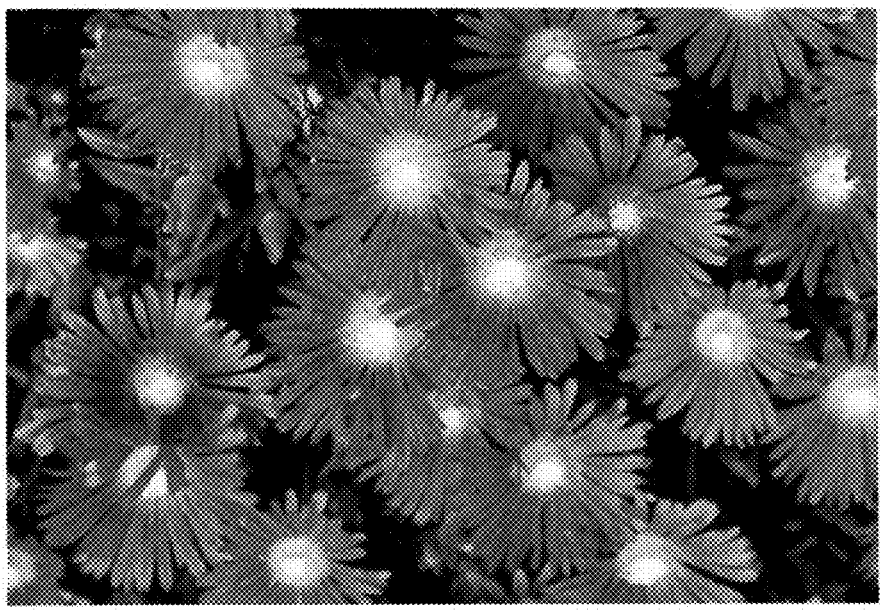
FIG. 2 shows a close-up of the flowers and young buds of a two-year-old plant.
Figure 3:
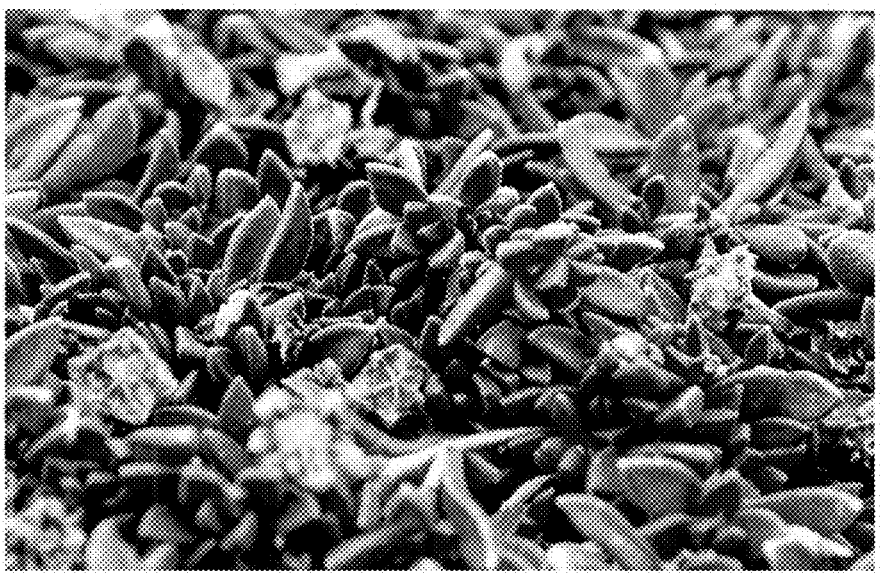
FIG. 3 shows a close-up of the winter foliage of a two-year-old plant.

The following is a detailed description of two-year-old plants of the new cultivar grown outdoors in a full sun trial garden with supplemental water and fertilizer as needed at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Delosperma* hybrid;

Cultivar denomination: 'Dancing Embers';

Parentage: The female parent is 'PJS01S'; the male parent is 'John Proffitt';

Asexual propagation: Terminal vegetative cuttings;

Root description: Thin, fibrous, freely branching; color near white depending on soil matrix;

Habit: Low sprawling mound; freely-branching; winter-hardy perennial; to about 60 cm wide and cm tall;

Foliage: Opposite; linear; succulent; with acute apex; truncate partially clasping base; entire margins; slightly concavo-convex; adaxial and abaxial surface glandular and slightly lustrous; to about 25 mm long, 8 mm wide slightly distal to center and 3.5 mm thick;

Leaf color: Adaxial and abaxial young and mature color between RHS 146D and RHS 145A in basal 3 to 4 mm, distally nearest RHS 137A; late fall, winter, and early spring color nearest RHS 187A in portions facing upwards toward direct sunlight, portion not facing direct sunlight between RHS NN137D and RHS 138A;

Venation: Veins not distinguishable from leaf;

Stem: Stolon; cylindrical; succulent; slightly lustrous; glabrous; glandular distally; to about 25 cm long and 2.5 mm diameter; branching at nodes;

Stem color: Distally in shaded or low light nearest RHS 145D, distally in higher light distally nearest RHS 182C with an undertone of nearest RHS 146D, proximally nearest RHS 161A;

Nodes: Average about 3 mm thick; average distance about 22 mm apart, greater distances distally and shorter at stem base; node color same as surrounding stem;

Branches: To about 17 cm long and 2 mm diameter; color proximally nearest RHS 161A, distally nearest RHS 145D in lower light and nearest RHS 182C with an undertone of nearest RHS 146D in higher light;

Petiole: Sessile;

Inflorescence: Single; radial; complete; perfect; actinomorphic; one to three flowers per node;

Flower bud: Cylindrical; upright; to about 16 mm tall, 8 mm diameter at apex, and 9mm diameter at calyx; petal color nearest RHS 72A in petal longitudinal center and nearest RHS 45B along petal margins; sepals nearest RHS NN137C distally and at base of hypanthium between RHS 146D and RHS 145A;

Bloom period: Beginning late May and continuing through at least September in Zeeland, Michigan;

Inflorescence lasting: Two to three days in fully open state; aspect upwardly;

Individual flower size: To about 52 mm across, 15 mm deep;

Petals: To about 40 per flower; linear; apex emarginate with one to two notches about 0.5 mm deep; base truncate; margin entire; highly lustrous metallic sheen adaxial and abaxial; slightly arcuate downwardly; to about 27 mm long and 4.5 mm across toward apex;

Petal color: When first open adaxial proximal one-third between RHS N75D and RHS 42D, distal two-thirds nearest RHS 42C; when first open abaxial base nearest RHS N75D, distally in the center nearest RHS NN78A and margins nearest RHS 46B; when mature adaxial proximal one-quarter nearest 77D, center one-half between RHS 44B and RHS 53B, and distal one-quarter between RHS 60A and RHS 60B; mature abaxial proximal one-quarter nearest RHS 76B, distally between RHS 77A and RHS N78A;

Petaloid: About 38 to 52; linear; narrowly acute apex; truncate base; entire margin; to about 12 mm long and 0.5 mm across, decreasing toward center;

Petaloid color: Adaxial and abaxial proximal portion nearest RHS 76A, central portion nearest RHS NN155D, and distal portion nearest RHS 171A;

Sepal: Five, in a single whorl; deltoid; succulent; with acute apex and truncate base; margin entire; adaxial and abaxial glabrous and slightly asperous; size variable, from 5 to 11 mm long and 4 to 7 mm wide at base;

Sepal color: Adaxial color nearest RHS 137A with a slight blush of nearest RHS N186C at base; abaxial nearest RHS 137A in the center and RHS 137C at the margin;

Pedicel: Cylindrical; glandular; succulent; to about 25 mm long and 3 mm diameter;

Pedicel color: Between RHS 146D and RHS 145B;

Gynoecium: Pentamerous; to about 11 mm long;

Pistil: Five; highly reduced, stigma and style indistinguishable; with stigmatic papillae; conic; to about 3 mm long and 2 mm across; color nearest RHS 146D;

Androecium: Quantity about 75 to 85;

*Filament.*—75 to 85; cylindrical; mostly straight; glabrous in exterior position filaments, puberulent in distal 1 mm on interior filaments; lustrous; to 4 mm long and 0.3 mm diameter; color variable, base between RHS 76D and RHS 76C, distally nearest RHS NN155D.

*Anther.*—Elliptical; to about 1 mm long and 0.5 mm across; color nearest RHS NN155B.

*Pollen.*—Abundant; color nearest RHS 11D.

Fruit: Penta-dehiscent capsule; to about 12 mm across and 7 mm tall; color at maturity nearest RHS 161C;

Seeds: To about 75 per flower; ellipsoidal; glabrous; about 0.7 mm long and 0.5 mm across; color variable, nearest RHS N199C, and between RHS 164C and RHS 164D;

Disease resistance: The new plant has not been observed to demonstrate either resistance or susceptibility to diseases and pests that might commonly be found on *Delosperma*.

Growth: The new plant has been shown to be winter hardy to at least USDA Zones 6 and tolerant of drought and high heat conditions.

I claim:

1. A new and distinct cultivar of *Delosperma* plant named 'Dancing Embers' as herein illustrated and described.

* * * * *